United States Patent [19]

Feiccabrino

[11] Patent Number: 4,495,372
[45] Date of Patent: Jan. 22, 1985

[54] PREPARATION OF MONO-NITRO AROMATIC COMPOUNDS

[75] Inventor: Joseph A. Feiccabrino, Naugatuck, Conn.

[73] Assignee: Uniroyal, Inc., Middlebury, Conn.

[21] Appl. No.: 403,450

[22] Filed: Nov. 5, 1982

[51] Int. Cl.³ .............................................. C07C 79/10
[52] U.S. Cl. .................................... 568/929; 568/928
[58] Field of Search ................................ 568/928, 929

[56] References Cited

U.S. PATENT DOCUMENTS 4,064,147  12/1977  Thelen et al. ................... 568/929 X
4,112,005   9/1978  Thiem et al. ......................... 568/929

FOREIGN PATENT DOCUMENTS 2453529  5/1976  Fed. Rep. of Germany ...... 568/929

OTHER PUBLICATIONS

Donaldson, The Chemistry and Technology of Napthalene Compounds, Edward Arnold, Ltt., London, 1958, pp. 145 to 148 and 163 to 166.

Primary Examiner—Leland A. Sebastian
Attorney, Agent, or Firm—John A. Shedden

[57] ABSTRACT

A process for mon-nitrating a plynuclear aromatic compound essentially in the absence of sulfuric acid and a solvent comprising adding nitric acid to a liquid aromatic compound wherein the molar ratio of nitric acid to the aromatic compound in from 0.75/1 ot 2/1 and the reaction temperature is from 50° to 100° C.

5 Claims, No Drawings

PREPARATION OF MONO-NITRO AROMATIC COMPOUNDS

The present invention relates to an improved batch process for the preparation of mono-nitro aromatic compounds essentially in the absence of a solvent and sulfuric acid using highly concentrated nitric acid at low $HNO_3$/aromatic compound ratios. In the prior art, nitration processes usually use a solvent in which the reactants are at least partially miscible and/or a combination of nitric acid and sulfuric acid. Some continuous processes are known wherein no solvents or sulfuric acid are employed.

U.S. Pat. No. 4,064,147 Dec. 20, 1977 (Thelen et al) teaches a continuous process for mono-nitrating aromatic compounds using a nitric acid to organic compound weight ratio of at least 3/1 which corresponds to a molar ratio of $HNO_3$ to organic compound of at least 4.26/1 in case of naphthalene.

U.S. Pat. No. 4,122,005 Sept. 5, 1978 (Thiem et al) discloses a continuous mono-nitration process for aromatic compounds in the absence of a solvent wherein the $HNO_3$ to aromatic compound molar ratio is from 4:1 to 50:1 and the $HNO_3$ is 40 to 68% concentration by weight.

It has now been found that mono-nitro aromatic compounds can be prepared readily and with high yields as a batch type process by reacting nitric acid with aromatic compounds in the absence of another acid such as sulfuric acid and in the absence of a solvent using low molar $HNO_3$/aromatic compound (AC) ratios as well as nitric acid having high concentration.

It is an object of the invention to provide a process for mono-nitrating aromatic compounds wherein no organic solvents are needed thereby eliminating the need for recovering and purifying the solvent.

It is a further object of the invention to provide a process for mono-nitrating aromatic compounds wherein there is no need for an acid other than nitric acid making the process less wasteful and more ecologically acceptable.

It is still a further object of the invention to provide a process for mono-nitrating aromatic compounds wherein there is provided a low ratio of nitric acid to aromatic compounds and high nitric acid concentrations which result in reduced amounts of aqueous waste and essentially eliminate the need to recycle the acid.

Another object of the invention is to provide a process for mono-nitrating aromatic compounds wherein the size of the reactor vessel may be kept smaller than for known processes.

It is a further object of the invention to provide a process for mono-nitrating aromatic compounds giving higher yields of mono-nitro aromatic compounds.

It is yet another object of the invention to provide a process for preparing high yields of 1-nitronaphthalene by nitrating naphthalene.

Generally, the process is carried out in the following manner: According to the invention the aromatic compound is charged to a suitable reactor and heated to a temperature somewhat above the melting point of said compound (in case of naphthalene ca. 81° C.). While agitating thoroughly, ntric acid is added over a period of from 15 minutes to 4 hours depending on the size of the batch.

The $HNO_3$/aromatic compound (AC) molar ratios may range from 0.75/1 to 2/1 or somewhat higher, preferably from 1/1 to 1.5/1 and usually from 1.2/1 to 1.4/1, and the concentration of the nitric acid employed may vary from 50 to 100 percent, although it is more advantageous to use 65 to 98 per cent, or more preferably 75 to 95 percent nitric acid.

Although a reaction temperature may be chosen between 50° and 100° C., it is preferred to conduct the process at 50° to 85° C., usually 55° to 70° C. Although the initial temperature of the aromatic compound may, for instance, be 81° C. or higher, the reaction may be gradually cooled to a lower process temperature usually while adding about the first 25 percent of the nitric acid. In many instances the nitration of the aromatic compound is substantially completed during the addition period of nitric acid, but, if necessary, the reactants may be held with agitation at the desired temperature for an additional time period ranging from 30 minutes to 3 hours. In any case, the total time of addition and post-addition reaction usually does not exceed 7 hours, and shorter periods such as 1 to 4 hours are usually sufficient. It should be noted that at higher $HNO_3$/AC ratios, reaction temperatures of about 50° to 75° C. are recommended, whereas at 1.5/1 and lower $HNO_3$/AC ratios the broad temperature range indicated above may be used. One skilled in the art will be aware that, in general, higher reaction temperatures favor shorter reaction time and vice versa. It is advised to provide efficient agitation throughout the reaction period.

Upon completion of the reaction, the mono-nitro product may be isolated by means well known in the art. For instance, if the melting point of the product is below room temperature it is usually feasible to separate the aqueous phase from the organic layer, remove trace nitric acid from the organic layer by washing with water, and dry the product. Further, purification of the product may be achieved by suitable distillation. If the product's melting point is 45° C. or higher, water and residual $HNO_3$ may be removed by distillation. Purification such as by crystallization may be carried out in known manners.

The above process is suitable for mono-nitration of aromatic compound such as naphthalene, 1- or 2-chloronaphthalene, 1-bromonaphthalene, methylnaphthalenes, ethylnaphthalenes, propylnaphthalenes, etc. In general, polynuclear aromatic compounds not readily oxidizable by nitric acid, naphthalenes carrying halo or $C_1$-$C_3$ alkyl substituents or a combination thereof, provided the aromatic compounds is not already fully substituted, may be nitrated in accordance with this invention. Also, polynuclear heterocyclic chemicals may be nitrated according to the process of this invention such as benzothiophene and naphthothiophene.

The process of this invention is particularly useful for the mono-nitration of naphthalene resulting in high 1-nitronaphthalene yields. It should be noted that at $HNO_3$/AC ratios of 1.2/1 and higher, essentially all of the aromatic compound is consumed eliminating in case of naphthalene, the sometimes bothersome recovery of the starting material. cl EXAMPLE 1

Preparation of 1-Nitronaphthalene

To a 2-liter resin flask equipped with a stirrer, thermometer, a dropping funnel, a $N_2$ sparge tube and a condenser vented to a caustic scrubber was added 1025 g (8.0 moles) naphthalene. The reactor contents were heated until the naphthalene became molten, at which time agitation was started, and the heating was stopped.

680 ml nitric acid (72.5% concentration, 10.0 moles) was introduced over a period of 3 hours. During the first 40 minutes of addition time the temperature was gradually reduced to about 62° C. and for the remaining addition period the reaction temperature was maintained between 50° and 60° C. By using reduced pressure (ca. 25 mm Hg) water and excess nitric acid were distilled off at 60°–75° C. for about 1.25 hours, and residual water and $HNO_3$ was driven off by sparging the molten reaction product with nitrogen gas while maintaining reduced pressure. During the 30 minutes sparging period the temperature was kept at 75°–80° C. The molten product (1408.5 g, 100% of theory) was removed from the reactor.

Assay:
Unreacted naphthalene—0
1-nitronaphthalene—95.7%
2-nitronaphthalene—4.3%
Other—Trace Following essentially the procedure of Example 1, additional experiments were carried out. The process conditions and results of these Examples (2–8) are summarized in Table I.

EXAMPLE 9

Additional aromatic compounds were treated following essentially the outline given in Example 1, resulting in good to excellent yields of the corresponding mononitrated compounds of 2-methylnaphthalene and 1-chloronaphthalene.

In the former case conversion was 97% and mononitro compounds assay was about 98%. In the latter case the corresponding results were 94% and 98%.

I claim:

1. A process for the preparation of mono-nitro polynuclear aromatic compounds comprising reacting a polynuclear aromatic compound with nitric acid in the absence of sulphur acid and in the absence of a solvent wherein the molar ratio of nitric acid to said aromatic compound is from 0.75/1 to 2/1.

2. A process according to claim 1 wherein the reaction temperature is maintained from 50° to 100° C.

3. A process according to claim 2 wherein said nitric acid is from 65 to 98% concentration.

4. A process according to claim 3 where the molar ratio of nitric acid to aromatic compound is from 1.2/1 to 1.4/1.

5. A process according to claim 4 wherein the reaction is from 1 to 4 hours.

* * * * *

TABLE I

Preparation of 1-Nitronaphthalene

| Ex. No. | NAP Moles | $HNO_3$ Conc. % | $HNO_3$/NAP Molar | Add'n Time, hrs. | Add'n Temp. °C. | Post-Add'n Time, hrs. | Post Add'n Temp. °C. | Conversion % | Assay, % ANN | BNN | OTHER |
|---|---|---|---|---|---|---|---|---|---|---|---|
| 2 | 8.0 | 90 | 0.75/1 | 1 | 100 | 3 | 100 | 63.7 | 87.9 | 6.1 | 6.0 |
| 3 | 8.0 | 90 | 0.9/1 | 2 | 80 | 2 | 80 | 79.7 | 90.4 | 7.5 | 2.1 |
| 4 | 8.0 | 75 | 1/1 | 2 | 78–50 | 3 | 50–60 | 93.6 | 90.1 | 3.5 | Trace |
| 5 | 9.75 | 68 | 1.07/1 | 1 | 86–70 | 3 | 70 | 97.9 | 94.0 | 4.7 | 1.3 |
| 6 | 7.78 | 90 | 1.1/1 | 1 | 80–65 | 5 | 65–70 | 98.3 | 89.7 | 5.7 | 4.5 |
| 7 | 8.0 | 86 | 1.36/1 | 4 | 78–50 | 2 | 50–60 | 100 | 90.0 | 6.5 | 3.5 |
| 8 | 8.0 | 68 | 2.04/1 | 3 | 76–50 | 1 | 50–60 | 100 | 84.3 | 4.9 | 10.8 |

Remarks:NAP: Naphthalene
NHO Conc.: Concentration of nitric acid
Add'n.: Addition (Time, etc.)
Assay: Composition of product
Conversion: Based on naphthalene
Ann: 1-nitronaphthalene
BNN: 2-nitronaphthalene
OTHER: dinitronaphthalenes, etc.
The above results confirm the applicability of the process parameter ranges stated.